US008046177B2

(12) United States Patent
Liu et al.

(10) Patent No.: US 8,046,177 B2
(45) Date of Patent: Oct. 25, 2011

(54) METHOD AND APPARATUS FOR DETECTING DAMAGE IN ARMOR STRUCTURES

(75) Inventors: Bao Liu, Cupertino, CA (US); Irene Li, Stanford, CA (US); Fu-Kuo Chang, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 389 days.

(21) Appl. No.: 12/060,799

(22) Filed: Apr. 1, 2008

(65) Prior Publication Data

US 2009/0043516 A1     Feb. 12, 2009

Related U.S. Application Data

(60) Provisional application No. 60/912,112, filed on Apr. 16, 2007.

(51) Int. Cl.
    *G01B 5/28*     (2006.01)
    *G01M 3/00*     (2006.01)
(52) U.S. Cl. ............................................. 702/35; 73/577
(58) Field of Classification Search .................... 702/35, 702/34, 36, 39, 42–43, 57–59, 64–66, 70–71, 702/73, 75, 79, 81, 84, 108, 125, 176, 179–183, 702/185, 188–195, 199; 2/455, 462, 465; 73/574, 577, 584, 588–589, 609–610, 618, 73/620, 624–625, 627–629, 632; 340/870.11, 340/870.15, 870.16, 870.18
See application file for complete search history.

(56) References Cited

U.S. PATENT DOCUMENTS

| 7,180,302 | B2 * | 2/2007 | Kelsey et al. ................. 324/525 |
| 7,596,078 | B2 * | 9/2009 | Beard et al. .................. 370/201 |
| 2006/0042396 | A1 * | 3/2006 | Qing et al. ...................... 73/786 |
| 2006/0079747 | A1 * | 4/2006 | Beard et al. ................... 600/407 |
| 2006/0283266 | A1 * | 12/2006 | Qing et al. ............... 73/862.041 |
| 2007/0018083 | A1 * | 1/2007 | Kumar et al. ............ 250/227.14 |
| 2009/0326834 | A1 * | 12/2009 | Sundaresan et al. ........... 702/34 |

OTHER PUBLICATIONS

Godinez-Azcuaga et al., Acoustic Techniques for the Inspection of Ballistic Protective Inserts in Personnel Armor, Sep./Oct. 2003, Sample Journal, pp. 1-8.*

(Continued)

*Primary Examiner* — Michael Nghiem
*Assistant Examiner* — Toan Le
(74) *Attorney, Agent, or Firm* — Innovation Counsel LLP

(57) ABSTRACT

Detection of damage in armor structures, using networks of piezoelectric transducers. In particular, piezoelectric transducers can be placed at various points on the armor structure, effectively creating a number of paths between pairs of transducers. Each of these paths can be queried by transmitting an ultrasonic stress wave from one transducer to the other, and analyzing changes in the stress wave. The signal from the received stress wave can be time gated to remove crosstalk, and the resulting time gated signal can be analyzed for characteristics of damage. For instance, if the time gated signal is sufficiently attenuated, it can be determined that the armor structure has sustained damage to at least that region traversed by this particular path.

21 Claims, 9 Drawing Sheets

OTHER PUBLICATIONS

Giurgiutiu et al., Embedded Non-Destructive Evaluation for Structural Health Monitoring, Damage Detection, and Failure Prevention, Mar. 2005, The Shock and Vibration Digest, vol. 37, No. 2, pp. 83-105.*

Shawn J. Beard, Amrita Kumar, Peter X. Qing, David C. Zhang & Joel Patterson, "A Smart Patch System for Monitoring of Bonded Reparis", International Workshop of Structural Health Monitoring 2005, Stanford University, 11 pp.

Xinlin P. Qing, Shawn J. Beard, Amrita Kumar & Robert Hannum, A real-time active smart patch system for monitoring the integrity of bonded repair on an aircraft structure, Institute of Physics Publishing, Smart Materials and Structures, Smart Mater. Struct. 15 (1006) N660N73, 2006 IOP Publishing Ltd, Printed in the UK.

* cited by examiner

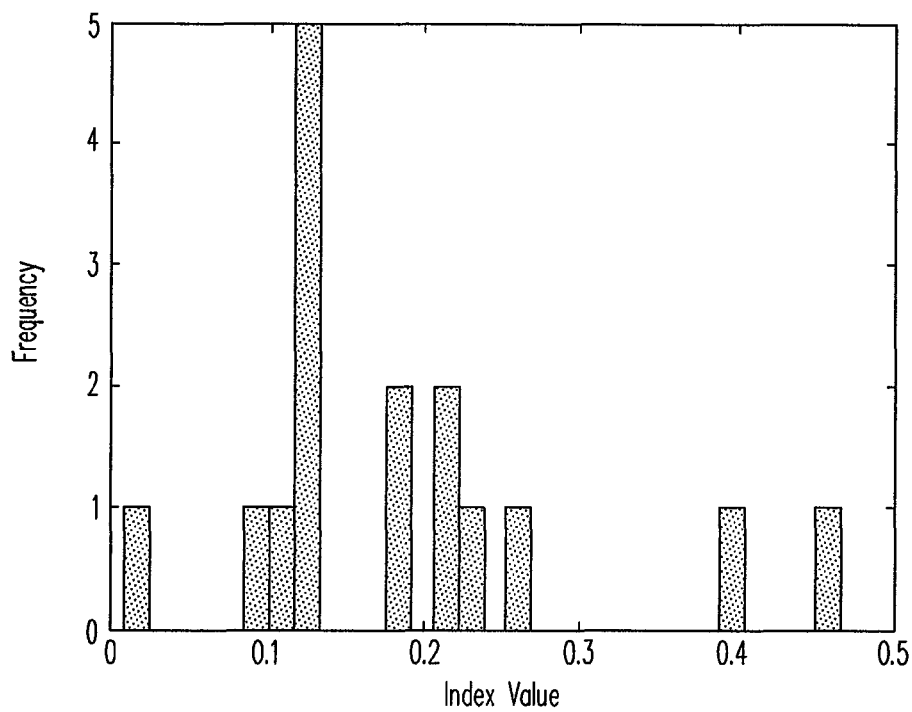
FIG. 3: Histogram of indices $I$ for a typical healthy body armor.
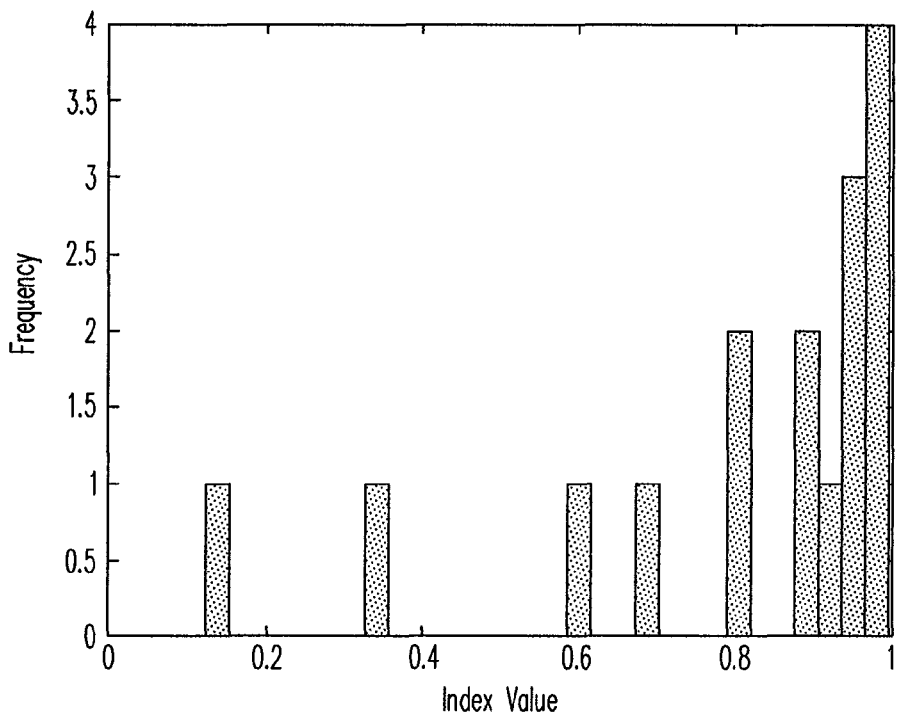
FIG. 4: Histogram of indices $I$ for a typical damaged body armor.

METHOD AND APPARATUS FOR DETECTING DAMAGE IN ARMOR STRUCTURES

CROSS-REFERENCE TO RELATED APPLICATION

This application claims the benefit of U.S. Provisional Patent Application Ser. No. 60/912,112, entitled "STRUCTURAL HEALTH MONITORING SYSTEM AND METHODS FOR USE," filed on Apr. 16, 2007, which is hereby incorporated by reference in its entirety.

BRIEF DESCRIPTION OF THE INVENTION

This invention relates generally to structural health monitoring. More specifically, this invention relates to the detection of damage in armor structures.

BACKGROUND OF THE INVENTION

Armor structures, such as ceramic plates used in body armor and other high-strength structures, are the subject of ongoing improvement efforts. More specifically, many pieces of modern body armor are composite structures. A major layer of the structure is the ceramic plate, which plays a decisive role in armor performance. The ceramic plate can be damaged by impact and this damage will affect subsequent armor performance. Detection of the damage is therefore very important. Accordingly, much current effort is focused on the reliable detection of damage in armor structures. Damage detection of armor structures is very important for the safety of protected people, vehicles or facilities. Maintaining the protection integrity of armor is vital to protection of life.

A major conventional damage detection method for inspecting armor employs X-ray imaging and visual inspection of the images. This method is generally inconvenient and of limited usefulness in the field. This damage detection procedure also requires well-trained personnel to inspect the images and precautions for radiation shielding. Thus, the cost of deploying such an inspection method is relatively high. Therefore, it is desirable to develop a method that is easy to use, does not adversely impact the weight or strength of the armor, and has a lower cost as compared to X-ray methods. It is further desirable to develop reliable armor damage detection methods that can be used in field conditions.

SUMMARY OF THE INVENTION

The invention can be implemented in a number of ways, including as a method and as a computer-readable medium.

In one embodiment, a method of determining the structural health of an armor structure comprises, in a system including an armor structure and a plurality of transducers affixed to the armor so as to define one or more paths between pairs of the transducers, transmitting an armor querying signal through the armor structure along one of the paths, the armor querying signal transmitted during a time period. The method further comprises detecting the armor querying signal at an end of the one of the paths so as to form a detected signal, the detected signal having a first portion detected during the time period and a second portion detected after the time period. The first portion of the detected signal is time gated, and it is determined whether a damage to the structure is present, the determining performed according to the second portion of the detected signal.

In another embodiment, a method of determining the structural health of an armor structure comprises, in a system including an armor structure and a plurality of transducers affixed to the armor so as to define one or more paths between pairs of the transducers, transmitting a first signal to a first transducer located at a first end of one of the paths, the first signal transmitted during a time period. The method further comprises detecting a second signal at a second transducer located at a second end of the one of the paths, the second end opposite to the first end along the one of the paths, the second signal detected after the time period. It is also determined whether damage to the armor structure is present along the one of the paths, the determining performed according to a comparison of the second signal to a predetermined baseline signal.

In another embodiment, a method of determining probability of detection POD values comprises, for a plurality of transducers affixed to a structure so as to define one or more paths along the structure between pairs of the transducers:

A) determining a value k of a characteristic dimension for a possible damage;
B) determining a number N of locations within a surface area defined by the plurality of transducers on the structure;
C) determining a number $n_k$ of the determined locations at which the possible damage having the value k of the characteristic dimension intersects one or more of the paths;
D) determining a probability of detection $POD_k = n_k/N$; and
E) successively incrementing k, and repeating B) through D) for each successively incremented value of k.

In another embodiment, a computer-readable medium stores instructions for carrying out a method with a system including an armor structure and a plurality of transducers affixed to the armor so as to define one or more paths between pairs of the transducers. The method comprises transmitting a first signal to a first transducer located at a first end of one of the paths, the first signal transmitted during a time period. The method also includes detecting a second signal at a second transducer located at a second end of the one of the paths, the second end opposite to the first end along the one of the paths, the second signal detected after the time period. The method further includes determining whether damage to the armor structure is present along the one of the paths, the determining performed according to a comparison of the second signal to a predetermined baseline signal.

Other aspects and advantages of the invention will become apparent from the following detailed description taken in conjunction with the accompanying drawings which illustrate, by way of example, the principles of the invention.

BRIEF DESCRIPTION OF THE DRAWINGS

For a better understanding of the invention, reference should be made to the following detailed description taken in conjunction with the accompanying drawings, in which:

FIG. 3 is a histogram of values of a damage detection index for an undamaged armor structure.

FIG. 4 is a histogram of values of a damage detection index for a damaged armor structure.

Like reference numerals refer to corresponding parts throughout the drawings.

DETAILED DESCRIPTION OF EMBODIMENTS OF THE INVENTION

In one embodiment, the invention relates to a method and apparatus for the detection of damage in armor structures, i.e., ceramic plate armor pieces. This method may overcome all the disadvantages of size, weight and cost, mentioned above. It includes: 1) lightweight built-in network sensors (which can also be actuators) which do not affect the strength and functionality of the structure, 2) a portable or handheld stand-alone actuation and data acquisition device for generation and collection of ultrasound signals generated by the built-in sensors/actuators, and 3) a software package that uses a specially developed process for signal noise reduction and damage detection. Unlike X-ray imaging methods and systems that may typically need well-trained personnel to operate and inspect the images, the processes of the present disclosure can automatically make the damage detection decision and indicate the condition of the armor structures. In addition, in an embodiment, the system is handheld and may be used in the field. The hardware and operation cost may also be lower than conventional X-ray systems.

Damage to ceramic plate armor (e.g., from impact) is known to manifest in characteristic ways. Ultrasound signals propagating in bulletproof armor structures may change considerably once the structure sustains damage. Embodiments disclosed herein utilize this observation to provide a method and apparatus for armor structure damage detection. The armor may have built-in lead zirconate titanate (PZT) piezoelectric transducers (or any other suitable transducer) as elastic wave actuators and sensors to excite the structure and to capture the structure response.

In particular, piezoelectric transducers can be placed at various points on the armor structure, effectively creating a number of paths between pairs of transducers. Each of these paths can be queried by transmitting an ultrasonic stress wave from one transducer to the other, and analyzing changes in the stress wave. The signal from the received stress wave can be time gated to remove crosstalk, and the resulting time gated signal can be analyzed for characteristics of damage. For instance, if the time gated signal is sufficiently altered, it can be determined that the armor structure has sustained damage to at least that region traversed by this particular path. As another example, indices are developed specifically for detection of damage in ceramic-type body armor.

The invention also contemplates further methods of analysis of the armor structure, such as determining a probability of detection (POD) curve for a particular transducer layout.

Figure 1:
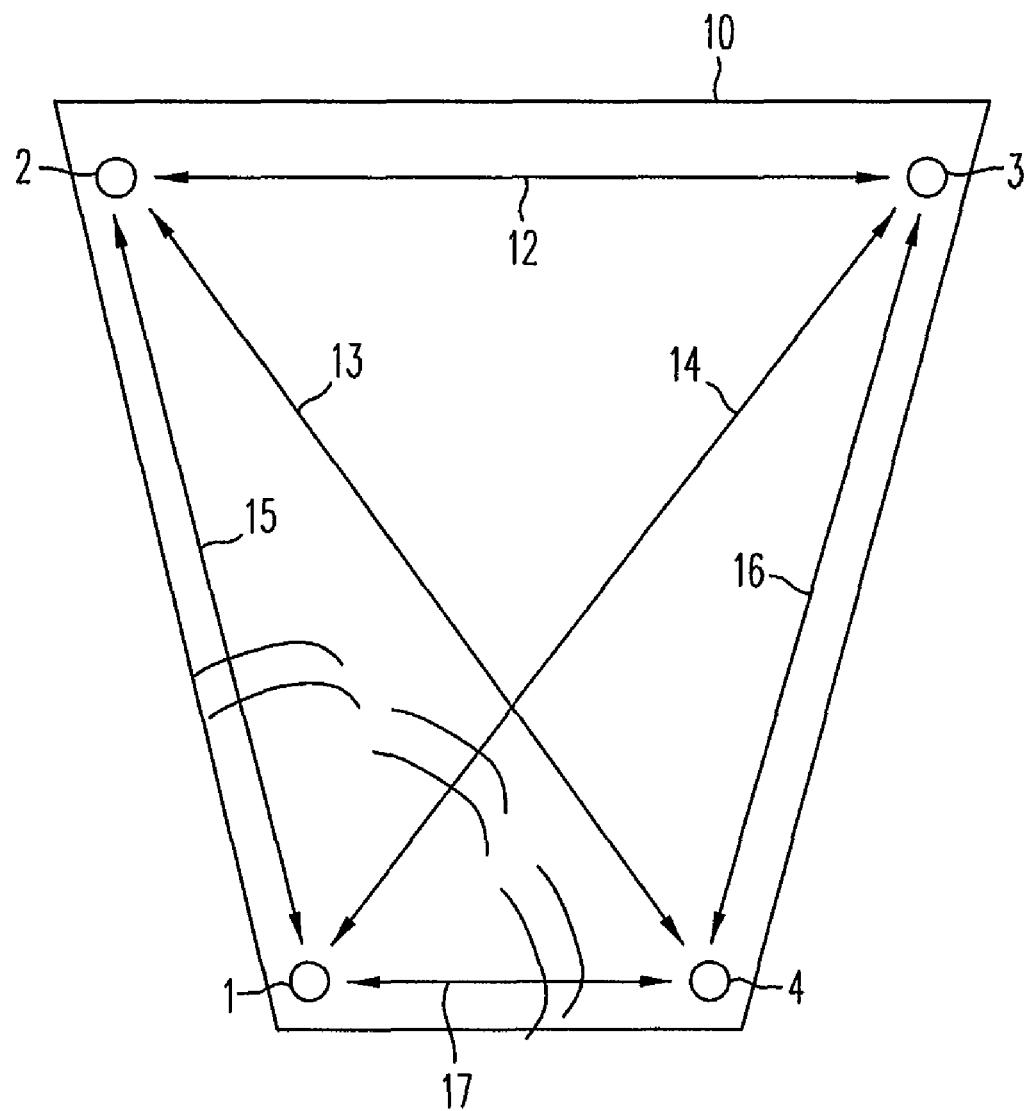
FIG. 1 conceptually illustrates an armor structure and attached (built-in) sensor network, constructed according to an embodiment of the present invention.

As shown in FIG. 1, a plurality of PZT element transducers (e.g., 1-4) is disposed on an armor structure 10. The armor structure 10 can be, for example, a ceramic body armor plate, or other type of armor meant for protecting persons or other assets in combat. The transducers 1-4 can be affixed to the armor structure 10 so as to transmit/receive stress waves along paths 12-17 in the structure 10. For instance, a first transducer (e.g., transducer 1) can be used as an actuator to input a stress wave to the structure, which propagates along paths 15, 14, and 17 as shown. The remaining PZT elements 2-4 function as sensors to detect and measure the propagated signals. By properly placing the transducers 1-4 on the structure 10, and alternating all the PZT elements on the structure as actuators and sensors, a diagnostic scan over effectively the entire surface of the structure 10 can be performed using various combinations of actuator-sensor paths. New techniques in each component of the system developed for the present application are disclosed.

Figures 2A, 2B:
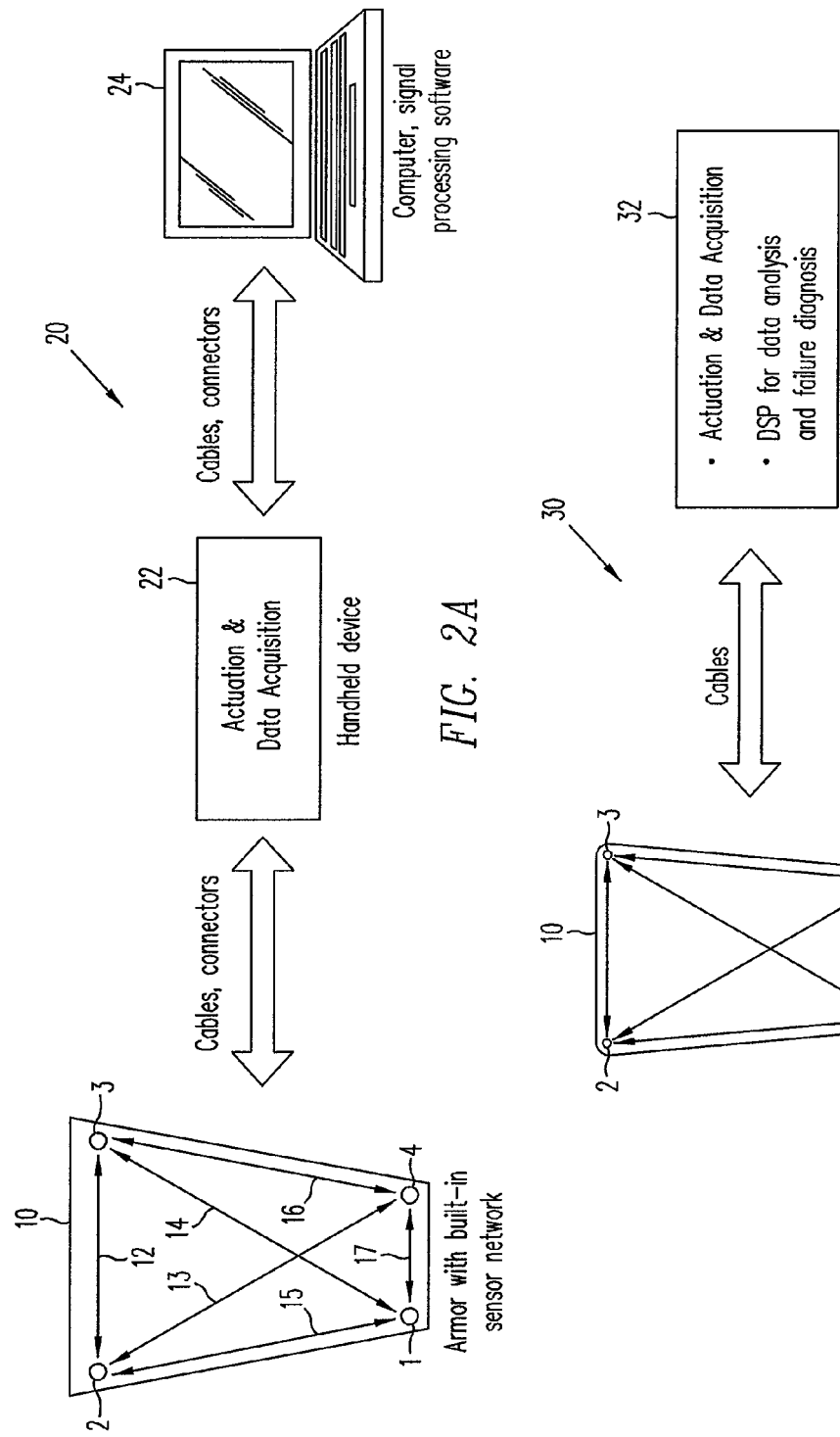
FIG. 2A illustrates a first embodiment of a damage detection system for armor structures according to the present invention.
FIG. 2B illustrates a second embodiment of a damage detection system for armor structures according to the present disclosure.

FIG. 2A illustrates a first embodiment of a damage detection system 20 for armor structures according to the present disclosure. System 20 includes a sensor embedded armor structure 10, a signal interface device 22 which interfaces between armor structure 10 and a computer 24 configured to run a software module that controls the interface device 22, determines actuation drive signal levels transmitted to transducers 1-4, analyzes received signals detected by transducers 1-4 when operated in sensor mode, and determines the location and severity of damage in the armor structure 10.

FIG. 2B illustrates a second embodiment of a damage detection system 30 for armor structures according to the present disclosure. In this embodiment, a hand held interrogation device 32 includes a digital signal processor (DSP) to implement the data analysis and damage detection. This DSP and the actuation and data acquisition circuits may be integrated into the single handheld device 32, such that no external computer is required to actuate transducers embedded in armor structure 10 or analyze the received signals resulting therefrom.

Sensors and Cables

Any necessary sensors and/or cables may be attached in any conventional manner known in the art. For example, a layer (e.g., a flexible circuit board) containing the sensors (e.g., transducers 1-4) attached thereto may be embedded or bonded to the armor structure 10 such that the transducers are effectively mechanically coupled to the structure 10 to generate and detect elastic wave signals. One may also use individually placed sensors for the same purpose but the installation may be less convenient and the signal quality may be variable and affected by the diversity among the individual sensors and the individual bonding conditions.

A connector (not shown) may be designed for electrically connecting the sensors on the structure with the signal interface device 12 or the handheld device 32. The connector is preferably small and does not affect the functionalities and strength of the structure. Preferably, the connector and cables that may be used are readily available commercially and capable of surviving in field conditions. Alternatively, the connectors may be custom designed for a particular desired application.

Actuation and Data Acquisition

In one embodiment, the handheld device 32 may use a battery power source since the signal propagation in the armor structures may often have relatively low energy loss and the system may not require high voltage to actuate the transducers. Besides actuation and data acquisition, handheld device 32 also has the capability to diagnose the sensors and the cables, such as through impedance analysis, using on-board digital signal processing (DSP) technology.

Damage Detection Methods

The systems of FIGS. 2A-2B can readily detect damage dealt to their armor structures 10. In one method, any transducer 1-4 can transmit stress waves along one or more of the paths 12-17, where they are detected by the remaining transducers 1-4. Attenuation of the detected signals indicates whether damage has been sustained along one or more paths.

With reference to FIGS. 2A-2B, a particular example can be given with respect to path 14, defined by transducers 1 and 3. Here, the actuation and data acquisition unit (of either handheld devices 22 or 32) can transmit an electrical actuation signal to a particular transducer, say transducer 1, causing it to transmit a stress wave through the structure and along path 14, where it is detected by transducer 3 and converted to an electrical signal. This latter electrical signal can, for present purposes, be deemed a received electrical signal. Damage along and close to the path 14 alters the stress wave, and thus also the received electrical signal.

The received electrical signal can then be sent to computer 24 or handheld device 32 to determine whether damage is present. The computer 24 or handheld device 32 can analyze received electrical signals and determine the presence of damage in any manner. Typically, the received electrical signals are first time gated to remove crosstalk. More specifically, it is known that interference from the electrical actuation signal sent to transducer 1 is detected at the other transducers, including transducer 3, producing an undesired electrical signal as part of the received electrical signal. However, because this undesired crosstalk signal is sent essentially instantaneously, while the stress wave signal takes time to propagate through the armor 10 along path 14, it can be observed that the electrical signal from transducer 3 will have an initial crosstalk portion, followed by a portion corresponding to the received stress wave. So long as the transducers 1, 3 are sufficiently far apart or the actuation signal sent to transducer 1 is sufficiently short, this crosstalk portion will not significantly overlap with the portion corresponding to the received stress wave. In this case, a time window, of duration equal to the duration of the actuation signal, can be applied to the received electrical signal, so as to time gate or effectively blank out any crosstalk. In this manner, the crosstalk portion of any received signal can be effectively disregarded.

Once crosstalk is removed or disregarded (whether via time gating or any other method, any of which are contemplated by the invention), the computer 24 or handheld device 32 can analyze the remaining received signal to determine whether damage exists along path 14. The invention contemplates any such analysis method. As one example, the time-gated received signal can be compared to a predetermined threshold. If the magnitude of the time-gated received signal never exceeds this predetermined threshold, it is determined that damage has occurred somewhere along path 14. As another example, the computer 24 or DSP of the handheld device 32 can store baseline signal features, to which the time-gated received signal can be compared. If the time-gated received signal is sufficiently different from the baseline signal, it is determined that damage has occurred somewhere along the path 14.

The comparison between the time-gated received signal and the baseline signal can be carried out in any manner. As one example, indices are developed specifically for detection of damage in ceramic plate structures such as body armor. The presence of damage is then determined according to sufficient changes in these indices. In one embodiment, indices are developed based on signal energy. Let $e_b^k$ be the energy of the gated signal of predetermined baseline data, and $e_c^k$ be that of the received signal respectively. Then, the index for the kth path can be defined as $$I_k = \frac{|e_b^k - e_c^k|}{e_b^k} \quad (1)$$

Suppose that there are K actuator-sensor paths in total. Then, for each scan, there will be K indices $I=\{I_1, I_2, \ldots, I_k \ldots, I_K\}$ with each index corresponding to one path.

Using the above indices, two damage indicators are designed based on the unique damage characteristics of ceramic armor structures. These characteristics differ from those of structures made from other materials such as metal and carbon fiber composite.

It has been observed that histograms of the indices $I=\{I_1, I_2, \ldots, I_k \ldots, I_K\}$ for undamaged or "healthy" armors differ considerably from those that have been damaged. FIG. 3 shows the histogram of the indices I for a healthy body armor, for which the signal change is mainly caused by temperature variations (10° C.) in the armor. It has elongated tail at the right.

In general, it was found that, for healthy body armor structures, the histogram of the indices resulting from environmental variation (mainly temperature) either has an elongated right tail or is symmetric. This implies that the "skewness" in this case is usually either positive or close to zero, where skewness can be defined as $$\text{Skewness} = \frac{\sum_{n=1}^{K}(I_n - \bar{I})^3}{(K-1)s^3} \quad (2)$$

where $\bar{I}$ is the mean of the indices $I=\{I_1, I_2, \ldots, I_k \ldots, I_K\}$, and s is the standard deviation of I.

FIG. 4 shows a histogram of the indices I for a damaged body armor. The changes shown in the received signals are caused by both damage and temperature variation (also 10° C.) in the armor. In contrast to FIG. 3, the histogram of FIG. 4 has an elongated left tail.

In general, as with FIG. 4, it was found that for damaged body armor structures, the histogram of the indices $I=\{I_1, I_2, \ldots, I_k \ldots, I_K\}$ has an elongated left tail. In other words, damage is reflected in a negative value of skewness (2). For armor with minor damage, the skewness is close to zero. It should be pointed out that the indices here reflect the signal changes caused by both the damage and the temperature variation but the former tends to dominate the signal changes.

The histogram shown in FIG. 4 is consistent with the brittle characteristics of ceramic plate armor. When subject to an impact (e.g., bullet impact or drop), the resulting damage to a brittle structure like ceramic armor usually will be large and will change the signals of most actuator-sensor paths. In FIG. 4, the index values of the affected paths are close to 1, and 8 paths among the total of 15 paths have an index value greater than 0.9.

From FIGS. 3 and 4, it can also be seen that for damaged armor, some indices are smaller than some of the indices of the healthy armor. However, because of the characteristics described above, the mean values of the indices (the center of the histogram) for the two cases are well separated. This observation can be utilized in damage detection.

Based on the above, two damage indicators for damage detection of the ceramic armor structure can be employed. The first, $T_1$, is the Mean of the Indices ($\bar{I}$ in equation (2) above), and the second, $T_2$, is the Skewness (2) of the Indices.

It has been found that for minor cracks, the indicators $T_1$ and $T_2$ are close to 0.5 and 0 respectively. On the other hand, for large temperature variation, e.g., 50° C. temperature difference, the indicators $T_1$ and $T_2$ could also have values close 0.5 and 0. Fortunately, in practice, armor with minor ceramic cracks is not considered as damaged. Therefore, the threshold for $T_1$ can be specified considerably larger than 0.5 while the threshold for $T_2$ can be specified considerably less than 0. In tests, the thresholds for $T_1$ and $T_2$ were set as 0.7 and −1.0, respectively, and an armor is considered damaged if $T_1 > 0.7$ and $T_2 < -0.8$. These thresholds may be adjusted for different designs of body armor structures.

As another example, the difference between the maximum amplitudes of the two signals can be used as the metric for determining the presence of damage. That is, if the difference between the maximum amplitudes of the two signals exceeds a predetermined amount, damage can be determined to have occurred. As another example, the difference in the total signal energies (e.g., total strain energies) can be used as the damage-determining metric. The invention contemplates the use of any comparison, and any comparison metrics, for determining damage according to a stored baseline signal.

The invention also contemplates the determining and storage of any baseline signal. It is often preferable to determine a separate baseline signal empirically for each path to be analyzed, as material properties and other characteristics can vary by path. The baseline signals are also preferably determined at environmental conditions representative of the conditions under which the damage-determining methods of the invention are expected to be carried out.

Test Results

Figure 5C:
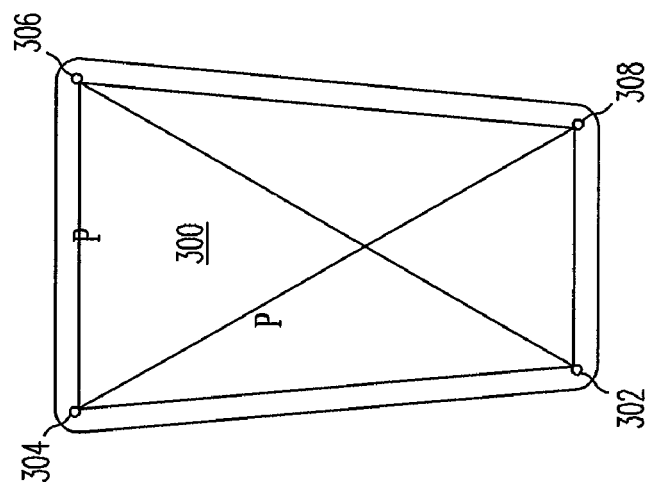
FIGS. 5A-5C conceptually illustrate test results for three damaged armor structures, and the transducer paths that were queried for damage.
Figure 5B:
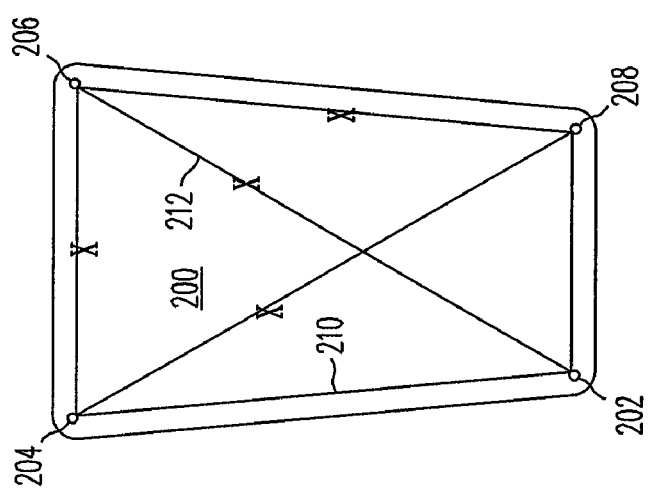
Figure 5A:
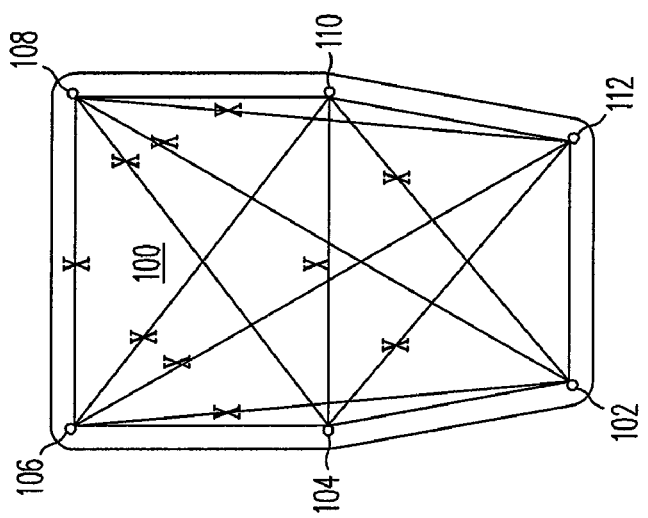

Methods of the invention were tested on three samples of bulletproof body armor. PZT transducers were affixed to three different pieces of body armor, as shown in FIGS. 5A-5C. As shown in FIG. 5A, transducers 102-112 were affixed to armor structure 100, which is a sample of Series No. 703289-32 bulletproof body armor. Similarly, as shown in FIGS. 5B-5C, transducers 202-208 were affixed to armor structure 200, which is a sample of Series No. 703289-18 bulletproof body armor, and transducers 302-308 were affixed to armor structure 300, a sample of Series No. 705532-1 bulletproof body armor.

Stress waves were transmitted along each of the paths shown in FIGS. 5A-5C (in FIGS. 5A-5C, each path is shown as a line). Stress waves were transmitted at frequencies of 200 kHz, 300 kHz, 400 kHz, and 500 kHz. For each path, an actuation signal was transmitted to one transducer, and the resulting detected stress wave was converted to an electrical signal, and time-gated according to the time window of the actuation signal. Specially developed indices of the time-gated detected electrical signal were then calculated based on the differences between the features of the current and the baseline signals. Damage was determined to be present along any path of which the indices exceeded the corresponding thresholds.

Each path was tested in the above-described manner in two different conditions. First, each path was tested when the armor structures 100, 200, 300 were in their original, undamaged condition. Each armor structure 100, 200, 300 was then damaged via drop testing, and each path was tested again. The paths which exhibited a significant difference between the two signals are marked with an "X" in FIGS. 5A-5B, designating paths for which it was determined that severe damage has occurred, and with a "P" in FIG. 5C. designating paths for which minor damage has occurred.

Figure 6A:
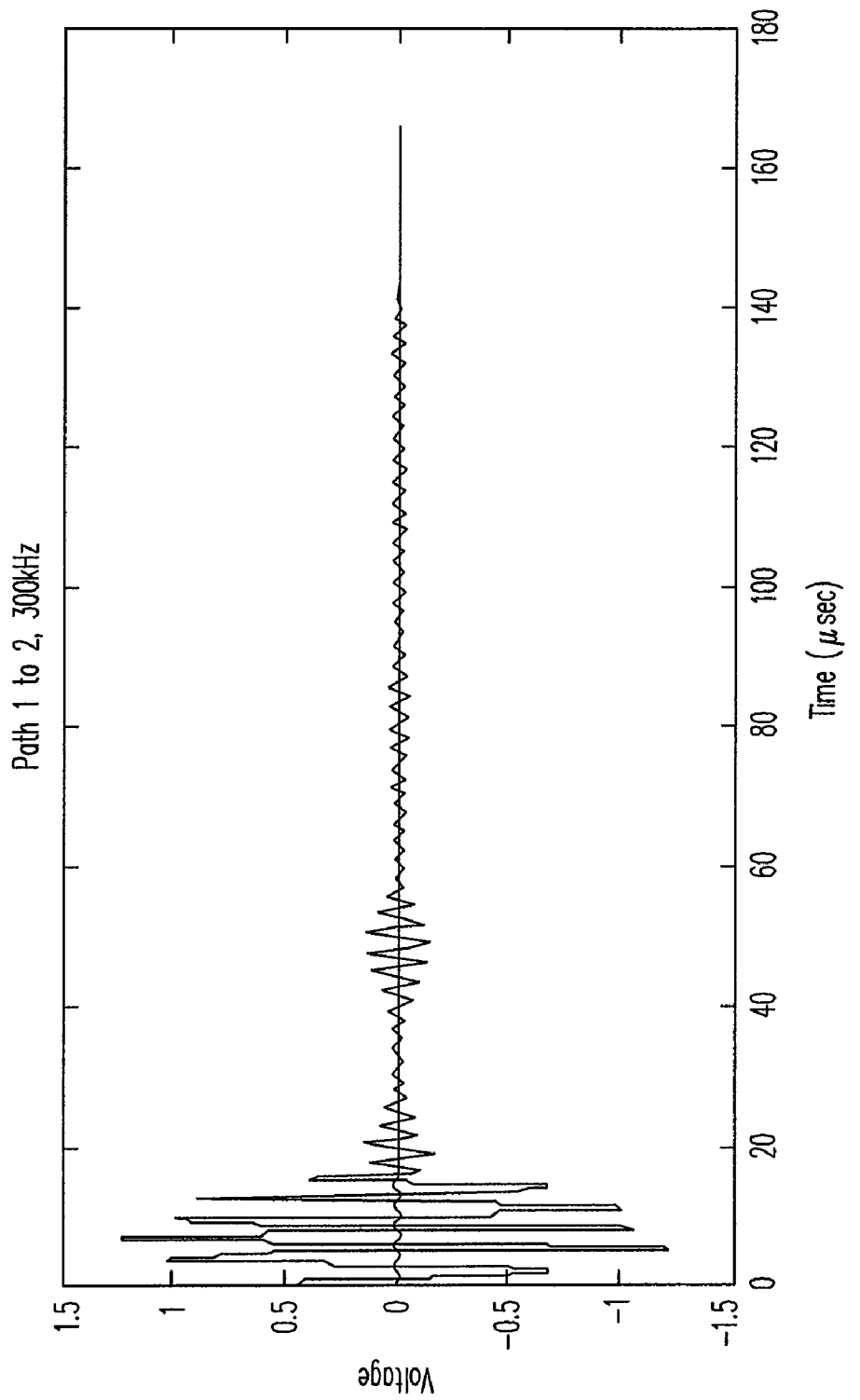
FIGS. 6A-6D are graphs of signals received from selected paths of FIG. 3B.
Figure 6B:
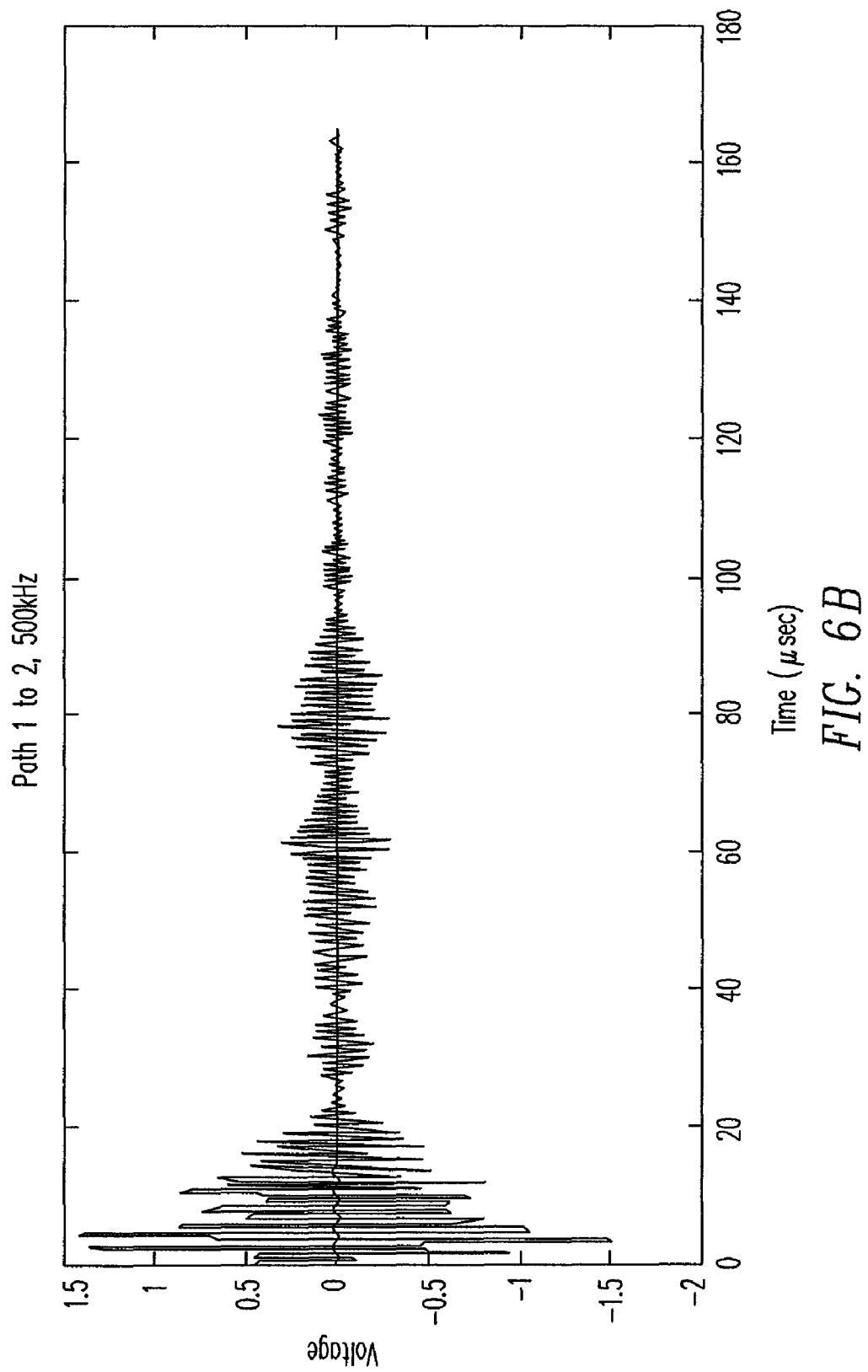

FIGS. 6A-6D are graphs of the signals received along paths 210 and 212 after drop testing. Path 212 is marked with an "X" while path 210 was not. In particular, FIG. 6A shows signals taken from undamaged path 210 for a 300 kHz actuation signal, while FIG. 6B shows signals taken from the same path 210 for a 500 kHz actuation signal. The actuation signal is 40 ms in duration. Accordingly, a 40 ms time window is applied to both signals, meaning that in both FIGS. 6A-6B, the detected signal prior to 40 ms is time gated out, or disregarded. In both FIGS. 6A-6B, it can be seen that there is a significant signal detected after 40 ms.

Figure 6C:
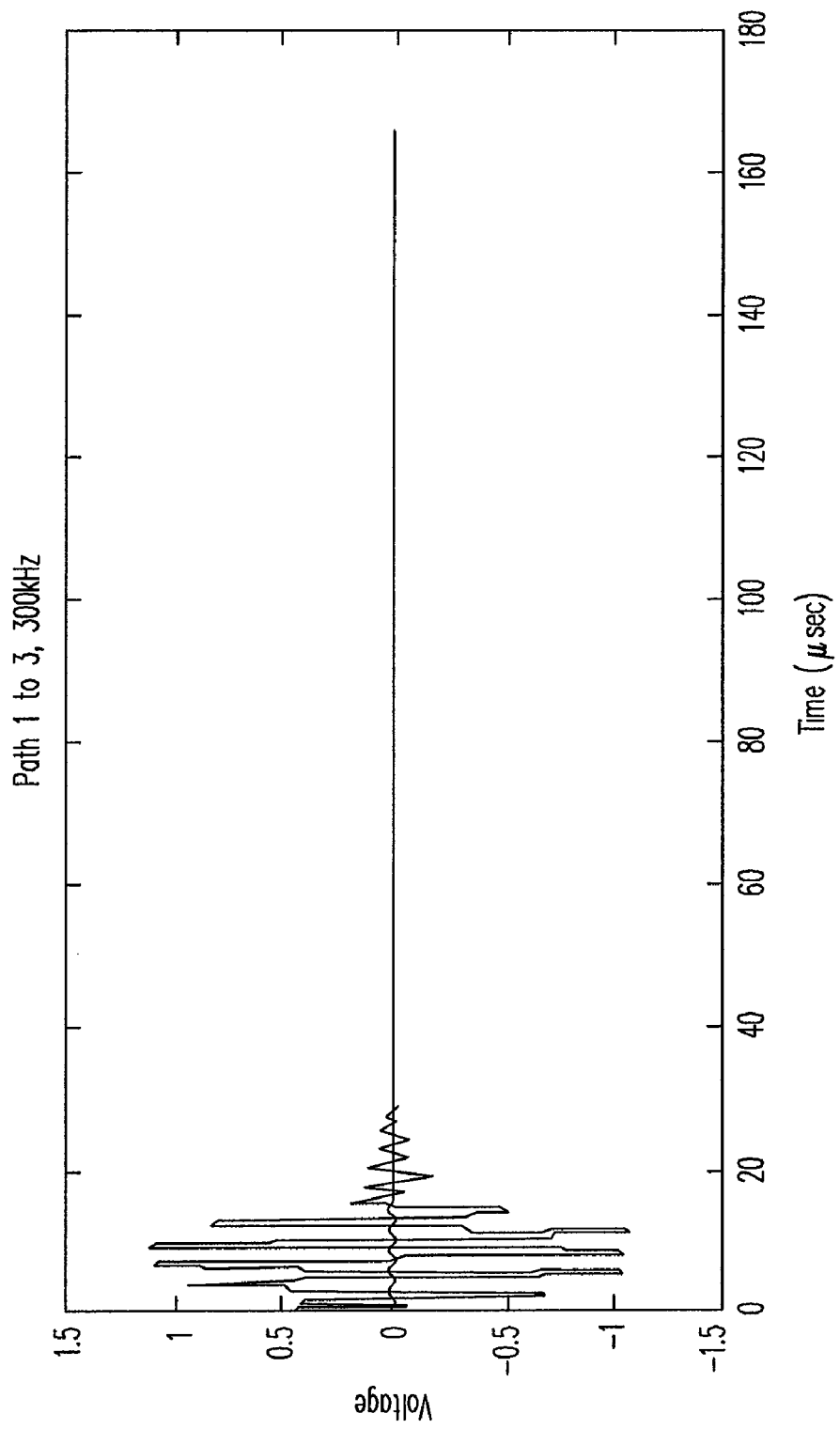
Figure 6D:
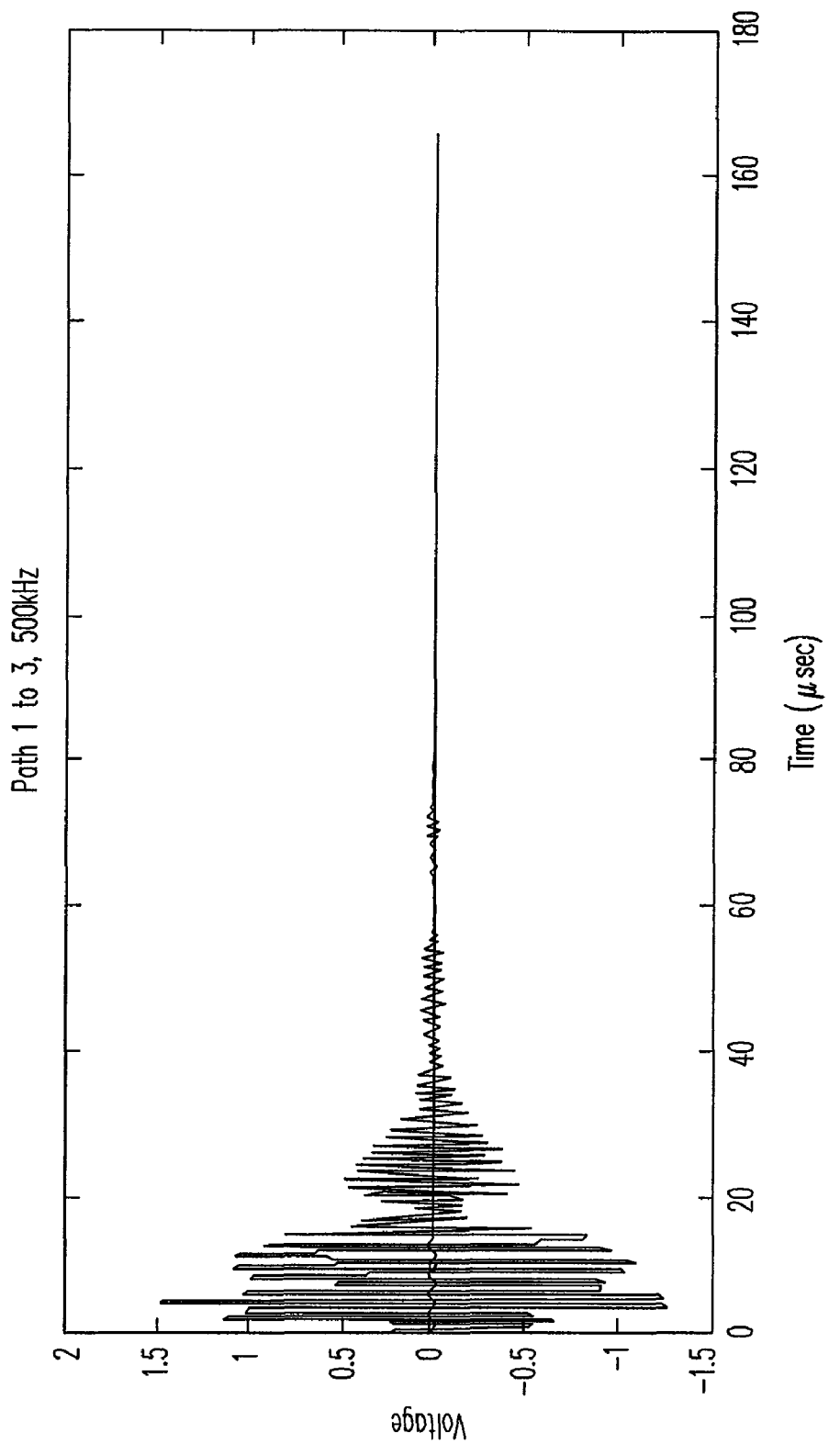

FIGS. 6C-6D show signals taken from damaged path 212 for 300 kHz and 500 kHz actuation signals, respectively. As above, a 40 ms actuation signal is applied, meaning that a 40 ms time window is applied to time gate the signals of FIGS. 6C-6D. Once these signals are time gated, it can be seen that no significant signal was detected along paths 212. The stress waves transmitted along path 212 and received after 40 ms elapsed were thus significantly (indeed, almost completely) attenuated relative to the stress waves transmitted along path 210. It can also be stated that the signals of FIGS. 6A-6B have considerable energy in the portions of those signals that were not time gated out, while the signals of FIGS. 6C-6D do not. It was thus determined that the armor 200 was damaged along path 212, but not along path 210.

Probability of Detection (POD)

Probability of detection (POD) is being introduced as a standard measurement for quantifying the reliability and robustness of built-in structural health monitoring systems. It has become common practice to quantify the reliability of flaw detection in terms of the probability of detection (POD).

POD tries to assess a minimum flaw size that will be reliably detected by a non-destructive testing (NDT) technique. This is best done by plotting the accumulation of flaws detected against the flaw size of all the flaws "detected," where "detected" may mean producing a signal response that exceeds some threshold. Ideally all flaws over some critical size will be detected and smaller flaws are not "detected". The tool most commonly used for POD description is the POD curve. The POD curve is useful in providing a reference method of quantifying the performance capability of an NDT procedure.

However, traditional POD curves are typically generated for single points and are obtained through extensive testing, which is not practical for every new structure and transducer array configuration. Structural health monitoring, e.g., the detection and location of defect damage in a structure, using an array of transducers, where the transducers may serve both as actuators and sensors, may require a modified or different approach. Experimental measurement may be expensive and yield answers based on poor statistics which may be caused, for example, by noise in the detection system, or a lack of sufficient test data; therefore attention has recently turned to modeling. To overcome this difficulty it is desirable to have a method to predict the POD for the entire structure, or any sub-region thereof, using merely the transducer coordinates, the operating actuator-sensor paths and the logic of a given damage detection process.

The present invention includes methods for generation of POD curves for armor structures. In particular, it is noted that the system of FIGS. 1 and 2A-2B can be employed to generate and utilize POD data, e.g., the transducers 1-4 can be used to create POD curves specific to the armor structure 10.

Figure 7:
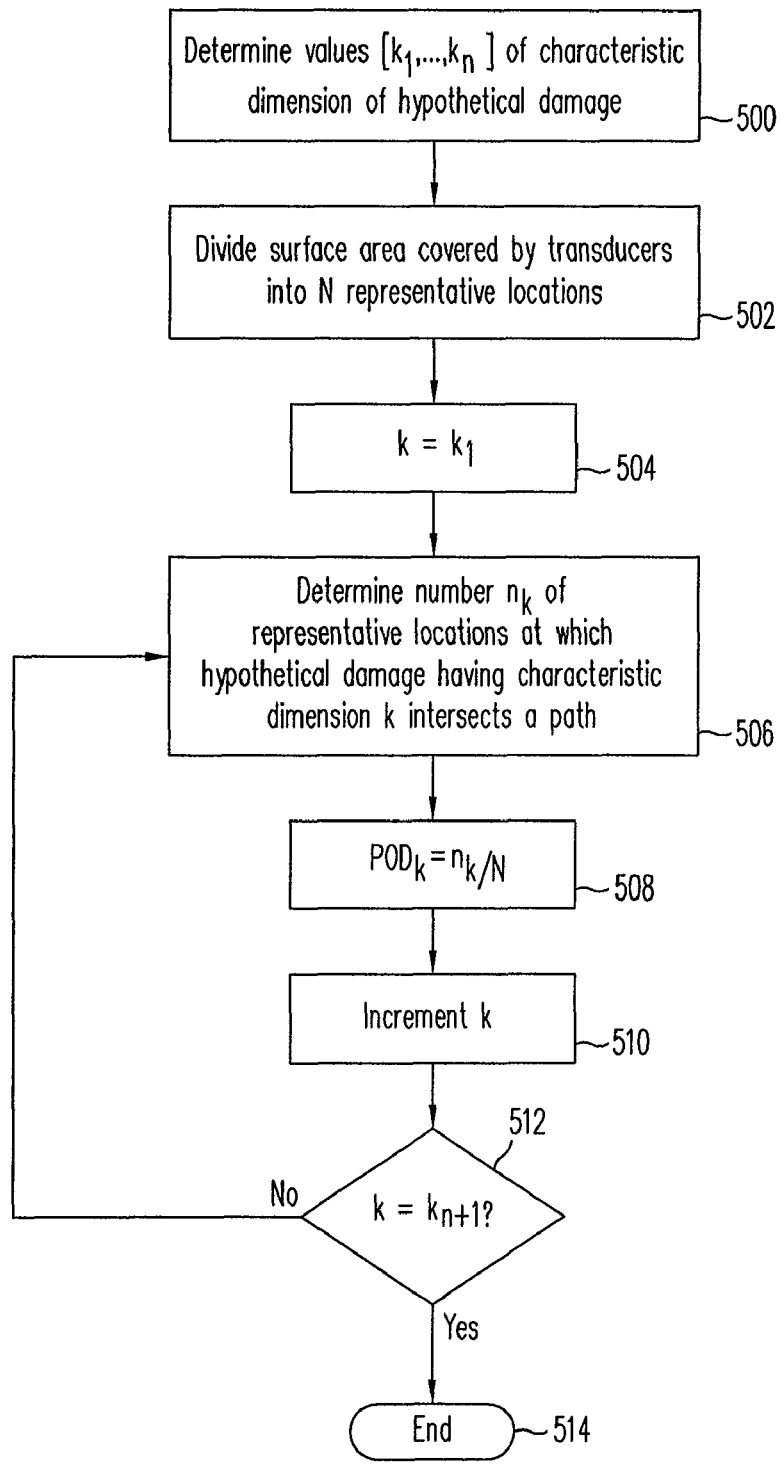
FIG. 7 is a flowchart of steps taken in determining probability of detection values for an armor structure of the present invention.

FIG. 7 describes steps taken in one embodiment for determining POD values for an armor structure of the present invention. In essence, damage is modeled as a particular shape having a characteristic dimension. For example, in ceramic armor structures, as in most brittle structures, damage often manifests as cracks. Accordingly, damage can be modeled as linear cracks, with crack length being the characteristic dimension. In other applications or conditions, it may be more desirable to model damage as circular holes or damage regions, in which case the characteristic dimension would be the radius of the damage regions.

Once a particular damage type is specified (e.g., cracks), the surface area covered by the transducers is divided into a number of different locations, and a hypothetical crack (or other damage) having the length (or other characteristic dimension) specified is centered at each location. Once the positions of these cracks are determined, the number of cracks that intersect a path is also found. The ratio of this number to the total number of locations yields the POD value for that particular crack length. Repeating this process for different crack lengths yields a POD curve describing probabilities that cracks of different lengths will be detected.

This process is described more fully with reference to FIG. 7. First, a particular damage type is specified, along with a number of values $[k_1 \ldots k_n]$ of the characteristic dimension of this damage type (step 500). The armor surface area covered by the transducers is then divided into N representative locations (step 502). These N locations are any locations representative of an "overall" POD for the transducer network, and in many instances is preferably the result of dividing the surface area defined by the perimeter of the transducer network into N equal portions.

The characteristic dimension k is then set to its first value, $k_1$ (step 504). The method then determines the number $n_k$ of the representative locations at which a hypothetical damage having characteristic dimension k intersects at least one path (step 506). For the case of a crack, the method would center a hypothetical crack at each representative location, and determine how many ($n_k$) of these cracks intersect an actuator-sensor path. The POD for that characteristic length $POD_k$ is then set equal to $n_k/N$ (step 508).

The value k of the characteristic length is then incremented to its next value (step 510), and a check is made whether $k=k_{n+1}$, i.e., whether a POD value has been calculated for every characteristic length (step 512). If not, the process returns to step 506. If all values $POD_k$ have already been determined, the process ends (step 514). The result of this process is a set of POD values $[POD_1 \ldots POD_k]$. These POD values can be graphed to yield a POD curve, or simply stored and used as desired.

One of ordinary skill in the art will realize that the invention encompasses variations on the above-described process for determining POD values. As described above, this process can be executed with different possible damages besides cracks. One of ordinary skill in the art will realize that any possible damage capable of being modeled with one or more characteristic dimensions can be so analyzed. One of ordinary skill in the art will also realize that the POD values $[POD_1 \ldots POD_k]$ can be used individually, or can be collectively used to generate a POD curve for the structure and transducer configuration analyzed.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, the methods of the invention contemplate identifying and disregarding crosstalk signals by time gating, use of any indices, or any other method. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A computer-implemented method of facilitating a determination of health of a structure, comprising:
   in a system including a plurality of transducers affixed to the structure so as to define one or more paths between pairs of the transducers, determining a probability of detection curve corresponding to probabilities that the plurality of transducers will detect differently sized damages to the structure, wherein the determining a probability of detection curve further comprises:
   A) determining a value k of a characteristic dimension for a possible damage;
   B) determining a number of locations N within a surface area defined by the plurality of transducers on the structure;
   C) determining a number $n_k$ of the determined locations at which the possible damage having the value k of the characteristic dimension intersects one or more of the paths;
   D) determining a probability of detection $POD_k = n_k/N$;
   E) successively incrementing k, and repeating B) through D) for each successively incremented value of k.

2. A computer-implemented method of determining health of a structure, comprising:
   in a system including a plurality of transducers affixed to the structure so as to define one or more paths between pairs of the transducers, transmitting a querying signal through the structure along one of the paths;
   detecting the querying signal at an end of the one of the paths so as to form a detected signal;
   repeating the transmitting and the detecting for each path of the one or more paths, so as to generate a plurality of detected signals; and
   determining whether a damage to the structure is present, the determining performed according to the plurality of detected signals;
   wherein the determining whether a damage to the structure is present further comprises:
     determining indices according to differences between energies of the detected signals and an energy of a predetermined baseline signal;
     determining a mean of the indices and a skewness of the indices; and
     comparing the mean of the indices to a first predetermined threshold, and the skewness of the indices to a second predetermined threshold.

3. The computer-implemented method of claim 2, wherein the determining whether a damage to the structure is present further comprises determining the presence of damage when the mean of the indices exceeds the first predetermined threshold and the skewness of the indices falls below the second predetermined threshold.

4. The computer-implemented method of claim 3, wherein the first predetermined threshold is approximately 0.7, and the second predetermined threshold is approximately −0.8.

5. The computer-implemented method of claim 2, wherein the indices I for each of the paths k are determined according to $$I_k = \frac{|e_b^k - e_c^k|}{e_b^k},$$

where $e_b^k$ is the energy of the predetermined baseline signal, and $e_c^k$ is the energy of the detected signal of path k.

6. The computer-implemented method of claim 5, wherein the skewness of the indices is determined according to $$\frac{\sum_{n=1}^{K}(I_n - \bar{I})^3}{(K-1)s^3},$$

where K is the total number of the paths, $\bar{I}$ is the mean of the indices I, and s is the standard deviation of I.

7. A computer-implemented method of determining health of a structure, comprising:
 in a system including a plurality of transducers affixed to the structure so as to define one or more paths between pairs of the transducers, transmitting a first signal to a first transducer located at a first end of one of the paths;
 detecting a second signal at a second transducer located at a second end of the one of the paths, the second end opposite to the first end along the one of the paths;
 determining whether damage to the structure is present along the one of the paths, the determining performed according to a comparison of the second signal to a predetermined baseline signal; and
 repeating the transmitting and the detecting for each path of the one or more paths, so as to generate a plurality of second signals;
 wherein the determining whether damage to the structure is present further comprises:
  determining indices according to differences between energies of the second signals and an energy of a predetermined baseline signal;
  determining a mean of the indices and a skewness of the indices; and
  comparing the mean of the indices to a first predetermined threshold, and the skewness of the indices to a second predetermined threshold.

8. The computer-implemented method of claim 7, wherein the determining whether damage to the structure is present further comprises determining the presence of damage when the mean of the indices exceeds the first predetermined threshold and the skewness of the indices falls below the second predetermined threshold.

9. The computer-implemented method of claim 8, wherein the first predetermined threshold is approximately 0.7, and the second predetermined threshold is approximately −0.8.

10. The computer-implemented method of claim 7, wherein the indices I for each of the paths k are determined according to $$I_k = \frac{|e_b^k - e_c^k|}{e_b^k},$$

where $e_b^k$ is the energy of the predetermined baseline signal, and $e_c^k$ is the energy of the detected signal of path k.

11. The computer-implemented method of claim 10, wherein the skewness of the indices is determined according to $$\frac{\sum_{n=1}^{K}(I_n - \bar{I})^3}{(K-1)s^3},$$

where K is the total number of the paths, $\bar{I}$ is the mean of the indices I, and s is the standard deviation of I.

12. A computer-implemented method of determining probability of detection POD values for a structure having a plurality of transducers affixed thereto, the method comprising:
 in a system including a plurality of transducers affixed to the structureso as to define one or more paths along the structure between pairs of the transducers:
 A) determining a value k of a characteristic dimension for a possible damage;
 B) determining a number of locations N within a surface area defined by the plurality of transducers on the structure;
 C) determining a number $n_k$ of the determined locations at which the possible damage having the value k of the characteristic dimension intersects one or more of the paths;
 D) determining a probability of detection $POD_k = n_k/N$; and
 E) successively incrementing k, and repeating B) through D) for each successively incremented value of k.

13. The computer-implemented method of claim 12, wherein the possible damage is a possible crack, and the characteristic dimension is a crack length.

14. The computer-implemented method of claim 12, wherein C) further comprises determining a number $n_k$ of the determined locations at which the possible damage having the value k of the characteristic dimension and having a characteristic orientation intersects one or more of the paths.

15. The computer-implemented method of claim 12, wherein E) further comprises successively incrementing k over a range of values $[k_1 \ldots k_i]$.

16. A non-transitory computer-readable medium storing instructions for carrying out a method with a system including a structure and a plurality of transducers affixed to the structure so as to define one or more paths between pairs of the transducers, the method comprising:
 determining a probability of detection curve corresponding to probabilities that the plurality of transducers will detect differently sized damages to the structure, wherein the determining a probability of detection curve further comprises:
 A) determining a value k of a characteristic dimension for a possible damage;
 B) determining a number of locations N within a surface area defined by the plurality of transducers on the structure;
 C) determining a number $n_k$ of the determined locations at which the possible damage having the value k of the characteristic dimension intersects one or more of the paths;
 D) determining a probability of detection $POD_k = n_k/N$;
 E) successively incrementing k, and repeating B) through D) for each successively incremented value of k.

17. A non-transitory computer-readable medium storing instructions for carrying out a method with a system including a plurality of transducers affixed to a structure so as to define one or more paths between pairs of the transducers, the method comprising:

transmitting a first signal to a first transducer located at a first end of one of the paths;

detecting a second signal at a second transducer located at a second end of the one of the paths, the second end opposite to the first end along the one of the paths;

determining whether damage to the structure is present along the one of the paths, the determining performed according to a comparison of the second signal to a predetermined baseline signal; and repeating the transmitting and the detecting for each path of the one or more paths, so as to generate a plurality of second signals;

wherein the determining whether damage to the structure is present further comprises:

determining indices according to differences between energies of the second signals and an energy of a predetermined baseline signal;

determining a mean of the indices and a skewness of the indices; and comparing the mean of the indices to a first predetermined threshold, and the skewness of the indices to a second predetermined threshold.

18. The non-transitory computer-readable medium of claim 17, wherein the determining whether damage to the structure is present further comprises determining the presence of damage when the mean of the indices exceeds the first predetermined threshold and the skewness of the indices falls below the second predetermined threshold.

19. The non-transitory computer-readable medium of claim 18, wherein the first predetermined threshold is approximately 0.7, and the second predetermined threshold is approximately −0.8.

20. The non-transitory computer-readable medium of claim 17, wherein the indices I for each of the paths k are determined according to $$I_k = \frac{|e_b^k - e_c^k|}{e_b^k},$$

where $e_b^k$ is the energy of the predetermined baseline signal, and $e_c^k$ is the energy of the detected signal of path k.

21. The non-transitory computer-readable medium of claim 20, wherein the skewness of the indices is determined according to $$\frac{\sum_{n=1}^{K}(I_n - \bar{I})^3}{(K-1)s^3},$$

where K is the total number of the paths, $\bar{I}$ is the mean of the indices I, and s is the standard deviation of I.

* * * * *